(12) United States Patent
Lurie (10) Patent No.: US 7,311,668 B2
(45) Date of Patent: *Dec. 25, 2007

(54) STRESS TEST DEVICES AND METHODS

(75) Inventor: Keith G. Lurie, Minneapolis, MN (US)

(73) Assignee: Advanced Circulatory Systems, Inc., Eden Prairie, MN (US)

( * ) Notice: Subject to any disclaimer, the term of this patent is extended or adjusted under 35 U.S.C. 154(b) by 357 days.

This patent is subject to a terminal disclaimer.

(21) Appl. No.: 11/051,345

(22) Filed: Feb. 4, 2005

(65) Prior Publication Data

US 2005/0126567 A1 Jun. 16, 2005

Related U.S. Application Data

(63) Continuation of application No. 10/251,080, filed on Sep. 20, 2002, now Pat. No. 6,863,656.

(51) Int. Cl.
*A61B 5/00* (2006.01)
*A61B 5/02* (2006.01)

(52) U.S. Cl. .............. 600/481; 600/484; 600/485; 600/500; 600/529

(58) Field of Classification Search ............... None
See application file for complete search history.

(56) References Cited

U.S. PATENT DOCUMENTS

| 6,631,716 B1 * | 10/2003 | Robinson et al. ...... 128/204.21 |
| 6,662,032 B1 * | 12/2003 | Gavish et al. .............. 600/323 |
| 6,863,656 B2 * | 3/2005 | Lurie ......................... 600/481 |

* cited by examiner

*Primary Examiner*—Robert L. Nasser
(74) *Attorney, Agent, or Firm*—Townsend and Townsend and Crew LLP (57) ABSTRACT

One method for diagnosing a cardiovascular-related condition in a breathing person comprises interfacing a valve system to the person's airway. The valve system is configured to decrease or prevent respiratory gas flow to the person's lungs during at least a portion of an inhalation event. The person is permitted to inhale and exhale through the valve system. During inhalation, the valve system functions to produce a vacuum within the thorax to increase blood flow back to the right heart of the person, thereby increasing blood circulation and blood pressure. Further, at least one physiological parameter is measured while the person inhales and exhales through the valve system. The measured parameter is evaluated to diagnose a cardiovascular condition.

27 Claims, 5 Drawing Sheets

STRESS TEST DEVICES AND METHODS

This application is a continuation of U.S. application Ser. No. 10/251,080, filed Sep. 20, 2002, now U.S. Pat. No. 6,863,656.

BACKGROUND OF THE INVENTION

This invention relates generally to the field of diagnostics, and in particular to the diagnosis of cardiovascular conditions. More specifically, the invention relates to systems and methods for stressing a patient's cardiovascular system and then measuring various physiological parameters in order to diagnose the patient's condition.

Cardiovascular ailments, such as high blood pressure, coronary artery disease, and the like pose a significant health threat to millions of individuals. The early and proper diagnosis of such ailments can be beneficial in placing the patient on the road to recovery. Over the years, a variety of techniques have been developed to diagnose such conditions. Some of these techniques involve stressing the patient's cardiovascular system by requiring the patient to physically exercise. For example, one common stress test is to place various monitors on the patient and then require the patient to run on a treadmill. As the patient's system is stressed, parameters such as the patient's blood pressure, heart rate and ECG are measured. These are compared against a set of generally accepted "normal" responses, and abnormal responses are observed based upon the set of "normal" values.

While such tests are generally acceptable, they are cumbersome and inconvenient. For example, they may require the patient to run on a treadmill while being connected to a variety of sensors. Moreover, many patients are not able to exercise, and the exercise itself limits the kinds of physiological data that can be acquired. For instance, various types of measuring equipment are not compatible with a patient running on a treadmill.

Hence, this invention is related to systems and methods for stressing the patient's cardiovascular system in a more convenient and friendly manner. Such systems and methods provide a wide range of advantages as set forth below.

BRIEF SUMMARY OF THE INVENTION

The invention provides various systems and methods for diagnosing a cardiovascular-related condition in a breathing person. In one exemplary embodiment, the method proceeds by interfacing a valve system to the person's airway. The valve system is configured to decrease or prevent respiratory gas flow to the person's lungs during at least a portion of an inhalation event. With the valve system coupled to the person, the person is permitted to inhale and exhale through the valve system. During inhalation, the valve system functions to produce a vacuum within the thorax to increase blood flow back to the right heart of the person, thereby increasing blood circulation and blood pressure. Further, at least one physiological parameter is measured while the person inhales and exhales through the valve system. This parameter is evaluated to diagnose a cardiovascular condition. Hence, such a method permits a person's cardiovascular system to be stressed, without having the person physically exercise.

In one aspect, the physiological parameter is measured in a base line state prior to permitting the person to inhale and exhale through the valve system. The measured physiological parameter in the base line state is then compared with the measured physiological parameter following inhaling and exhaling to facilitate diagnosis. Further, such measurements may be compared with normal or expected responses, i.e. with historical data from healthy individuals.

Conveniently, the valve system may be incorporated into a facial mask that is coupled to the person's face. Further, the valve system may include a pressure responsive inflow valve having an actuating pressure in the range from about 0 cm $H_2O$ to about −50 cm $H_2O$. In some cases, the actuating pressure may be increased or decreased over time and the physiological parameter re-measured. Further, the actuating pressure may be increased or decreased based on the previously measured physiological parameter.

In some aspects, the valve system may be further configured to prevent or decrease exhaled gases from exiting the person's lungs during at least a portion of an exhalation. Also, the physiological parameter may be measured following an exhalation.

One particular feature is that the physiological parameter may be measured by an imaging or mapping technique, such as by an ECG, by echo-imaging of the heart, by imaging of radio-labeled markers in the blood, by MRI imaging, by CT imaging, by imaging of markers for cardiac ischemic, and the like. Use of many of these imaging or mapping techniques is possible during the stress test since the person needs only to be coupled to the valve system and is not required to physically exercise during the test. Use of the valve system also permits a wide range of parameters to be measured, such as blood pressure, expired $CO_2$, heart rate, air flow and pressure through the airway and lungs, oxygen saturation, blood levels of $O_2$, blood lactate, blood pH, tissue lactate, tissue pH, body temperature, and the like.

To enhance the effect of the valve system, one or more substances may be introduced into the person to stress the person's heart. Such substances may be injected into the person's blood stream (such as by use of a needle), may be delivered orally, may be inhaled, or the like. For example, the substance may comprise a volume load of saline solution that is injected into the person's blood stream to stress the person's system. As another example, the substance may comprise nitroglycerine that is injected into the person to lower the person's blood pressure. Other drugs that may be used to stress the heart include adenosine, adrenaline, dobutamine and the like.

In another embodiment, the invention provides an exemplary system for diagnosing a cardiovascular-related condition in a breathing person. The system includes a valve system that is capable of being coupled to the person's airway. The valve system is configured to decrease or prevent respiratory gas flow to the person's lungs during at least a portion of an inhalation event to produce a vacuum within the thorax to in turn increase blood flow back to the right heart of the person. In so doing, blood circulation and blood pressure is increased. The system also includes a monitoring system to monitor changes in at least one physiological parameter while the person inhales and exhales through the valve system. In this way, the person's cardiovascular system may be stressed on monitored simply by coupling the valve system to the person's airway and measuring the parameters.

In one aspect, the monitoring system includes a computer for evaluating the measured parameter to diagnose a cardiovascular condition. Conveniently, at least a portion of the monitoring system may be physically incorporated into the valve system. The monitoring system may also include a controller to change the configuration of the valve system over time to vary the level of inspiratory impedance. For example, the controller may be configured to change the configuration of the valve system based on the measured parameters.

In a further aspect, the valve system may be configured to prevent or decrease exhaled gases from exiting the person's lungs during at least a portion of an exhalation. Further, the valve system may be incorporated into a facial mask that is configured to be coupled to the person's face. The valve system may conveniently include a pressure responsive inflow valve that has an actuating pressure in the range from about 0 cm $H_2O$ to about −50 cm $H_2O$. Such a valve permits gases to flow to the person's lungs during a latter portion of an inhalation event in order to provide sufficient ventilation.

In one particular aspect, the monitoring system may comprise an imaging or mapping system. Examples of systems that may be used include an ECG system, a heart echo-imaging system, a radio-labeled marker imaging system for measuring makers in the blood, an MRI imaging system, a CT imaging system and a cardiac ischemic imaging system. Further, the monitoring system may use a wide range of sensors, such as blood pressure sensors, expired $CO_2$ sensors, heart rate sensors, air flow and pressure sensors, oxygen saturation sensors, $O_2$ blood level sensors, blood lactate sensors, blood pH sensors, tissue lactate sensors, tissue pH sensors and body temperature sensors.

DETAILED DESCRIPTION OF THE INVENTION

The invention provides various systems and methods to facilitate the measurement of one or more physiological parameters while a person's cardiovascular system is being stressed. The stress tests of the invention may be used when diagnosing a wide range of cardiovascular conditions, such as coronary artery disease, high blood pressure, pulmonary hypertension, cardiac function, severity of peripheral vascular disease, integrity of certain autonomic nervous system reflexes (including the carotid-baro reflex and the vagovagal reflex), intracardiac shunting of blood, and the like.

To stress the cardiovascular system, the invention may utilize some type of inspiratory impedance, at one or more predetermine levels, to increase venous blood flow to the heart, thereby increasing overall circulation and blood pressure. Such a perturbation of the normal physiological system of the body may be assessed by concurrent physiological monitoring. Further, the level of inspiratory impedance, and the way it is altered, may vary. For example, the level of impedance may vary by performing an automatic step-up or step-down of impedance, or it may vary depending upon physiological feedback.

To prevent or impede respiratory gases from flowing to the lungs, a variety of impeding or preventing mechanisms may be used, including those described in U.S. Pat. Nos. 5,551,420; 5,692,498; 6,062,219; 5,730,122; 6,155,257; 6,234,916 and 6,224,562, and in U.S. patent application Ser. No. 10/224,263, filed on Aug. 19, 2002 ("Systems and Methods for Enhancing Blood Circulation"), Ser. No. 09/966,945, filed Sep. 28, 2001 and Ser. No. 09/967,029, filed Sep. 28, 2001, the complete disclosures of which are herein incorporated by reference. The resistance to the inflow of respiratory gases may be set between about 0 cm $H_2O$ and about 50 cm $H_2O$ and may be variable or fixed as described above.

Because the person's system may be stressed without requiring physical exercise, monitoring of a wide range of physical parameters or conditions may be accomplished in a more convenient manner. For example, monitoring during the stress test may include, but is not limited to, ECG, blood pressure, echo-images of the heart (such as with an ultrasonic transducer or catheter), radio-labeled markers to visualize blood flow, MRI-imaging, CT imaging, measurement of expired $CO_2$, heart rate, air flow and pressure through the airway and lungs, oxygen saturation and/or blood levels of $O_2$, blood lactate, blood pH, tissue lactate, tissue pH, markers for cardiac ischemic (including tissue and serum creatinine phospho-kinase, serum troponin, serum adenosine—that may all be measured non-invasively or with minimal invasive techniques), temperature, and the like. In some cases, the imaging may need to be gated based upon the respiratory rate, or motion associated with the change in the position of the heart and other body structures (such as when taking MRI or CT images). Further, the valve system permits measurements to be made while the person is standing, sitting or lying down.

Hence, the valve may be configured to decrease intrathoracic pressures relative to both atmosphere pressures and extrathoracic pressures during diagnosis. Its use results in a greater vacuum in the thorax relative to the rest of the body during an inhalation maneuver. This forces more blood back to the chest, thereby increasing blood available for the heart beat. This results in a greater organ perfusion and thus stresses the cardiovascular system in a manner similar to performing exercise.

Conveniently, such valve systems may be incorporated into a facial mask to facilitate coupling of the valve system to the person's airway. Before actuating the valve system, the physiological measures may be made in a baseline state. The valve system may then be actuated or coupled to the airway and measurements taken while the person is breathing through the valve system (which functions to stress the person's cardiovascular system). In some embodiments, the valve system may be connected to or be able to communicate with monitoring systems to record, either directly or remotely from a transmitted signal, a wide variety of diagnostic information. These measurements may be taken before, during and after performing the stress test. The level of inspiratory impedance (plus or minus a small decrease of expiratory impedance) may be varied over a wide range of pressure using designs described in the above referenced patents and applications.

In addition to the use of the valve system, or as an alternative to the valve system, one or more substances may be introduced into the person to stress the person's heart. Hence, in some embodiments, the person's system may be stressed both by the impedance provided by the valve system while breathing and by the substance that is introduced into the patient. These substances may be introduced at one or more times, and using one or more techniques. For example, such substances may be injected into the person's blood stream (such as by use of a needle), may be delivered orally, may be inhaled, or the like. Further, the substances may be introduced before, during and/or after the valve system is coupled to the person. For example, the substance may comprise a volume load of saline solution that is injected into the person's blood stream to stress the person's system. As one example, the volume of saline solution may be in the range from about 500 cc to about 1,000 cc. As another example, the substance may comprise nitroglycerine that is injected into the person to lower the person's blood pressure. Other drugs that may be used to stress the heart include adenosine, adrenaline, dobutamine and the like.

Figure 1:
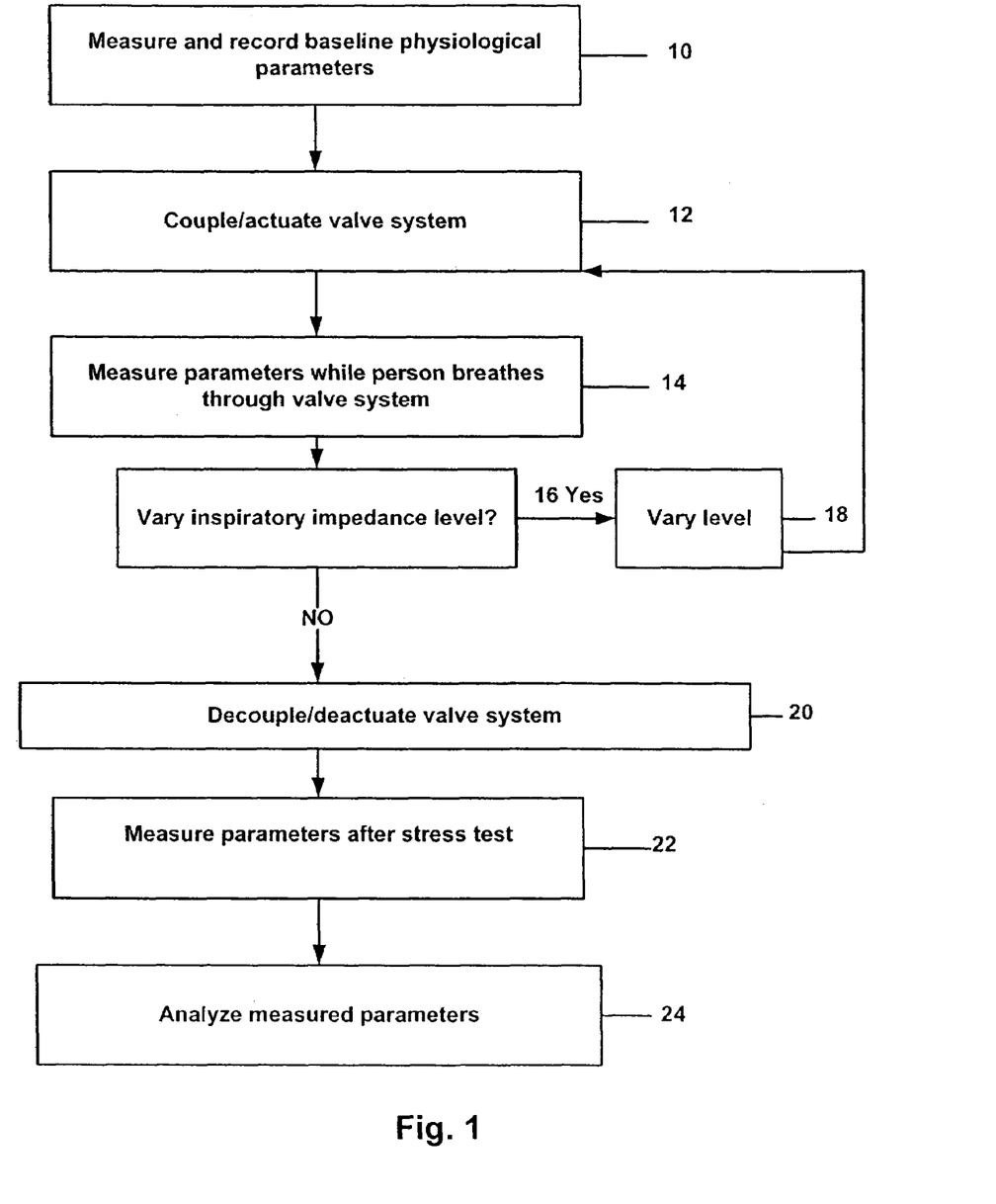
FIG. 1 is a flow chart illustrating one method for diagnosing a cardiovascular-related condition according to the invention.

Referring now to FIG. 1, one method for diagnosing cardiovascular-related conditions will be described. As shown in step 10, baseline physiological parameters may be measured and recorded. The baseline parameters are preferably taken before any stressing of the person's cardiovascular system. These parameters may comprise any of those previously described. Conveniently, these measurements may be stored in a computer and used for later analysis when comparing subsequent measurements.

The method also involves the step of coupling a valve system to the patient's airway as shown in step 12. This may be performed prior to taking any baseline measurements, provided the valve system is not actuated, or after the baseline measurements have been taken. If before, the valve system may simply be actuated when ready to begin stressing of the person's system. As the person breathes through the valve system, various physiological parameters are measured and recorded as shown in step 14. While breathing through valve system 200, the augmentation of pressures within the thorax increases venous blood flow to the hear, to increase overall circulation and blood pressure. As previously described, a substance may also be introduced into the person to increase the amount of stress on the person's system. One advantage of such a method is that measurements may be made using equipment that have typically been incompatible with stress tests. For example, the person may be imaged in a MRI or CT imaging device while breathing through the valve system. Echo images of the heart may also be taken while breathing through the valve system. Further, other measurements may be taken as previously described.

In some cases, it may be desirable to vary the inspiratory impedance level as shown in step 16. This may be the level of inspiratory impedance, expiratory impedance or both. In such cases, the level of impedance may be varied as illustrated in step 18, and the process reverts back to step 14 where the parameters are measured with the modified settings. The decision to vary the impedance may be made based on measurements previously recorded. For example, the computer may be programmed to evaluate the measured parameters over time and to send one or more signals to the valve system to change the impedance based on the analysis. Alternatively, the impedance may automatically vary depending on a certain routine. For example, the computer could control an automatic step-up or step-down of impedance. This variance could also be accomplished manually. Techniques for varying the impedance level are described in the previously mentioned patents and patent applications.

Once the appropriate measurements have been taken, the valve system may be decoupled or deactuated as shown in step 20. Optionally, measurements may also be taken after competition of the stress test as shown in step 22. With the measurements taken, an analysis of the measured parameters may be made as shown in step 24. These parameters may be measured against themselves, e.g., the change in blood pressure may be evaluated before, during and after the stress test, and/or against a set of historical data. Such historical data may have expected "normal" responses or ranges of normal responses that are compared against the measured data. If outside of the expected normal ranges, the comparison may be flagged for further consideration. In this way, a variety of cardiovascular conditions or problems may be evaluated in a convenient and more efficient manner.

Figure 2:
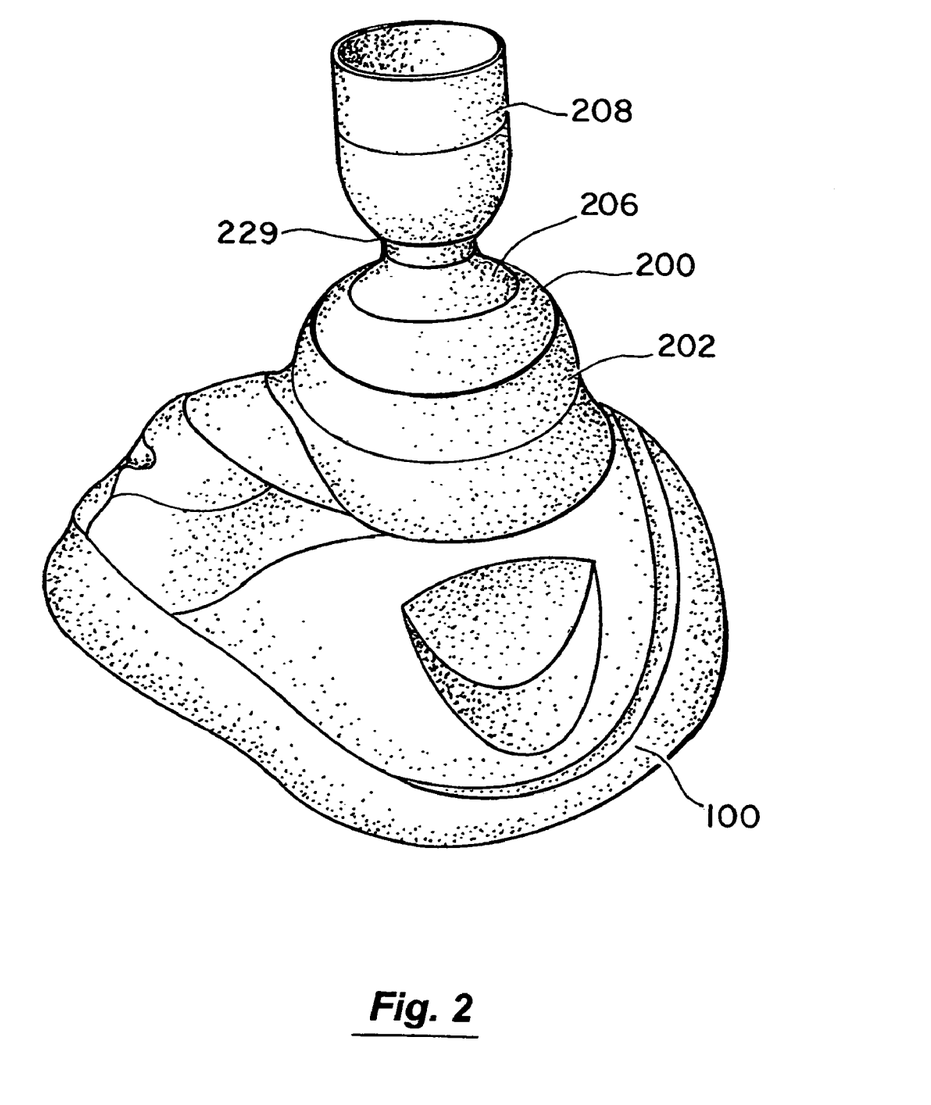
FIG. 2 is a perspective view of one embodiment of a facial mask and a valve system that may be used to facilitate a diagnosis according to the invention.

FIG. 2 illustrates one embodiment of a facial mask 100 to which is coupled a valve system 200. Mask 100 is configured to be secured to a patient's face so as to cover the mouth and nose. Mask 100 and valve system 200 are examples of one type of equipment that may be used to stress a person's cardiovascular system. However, it will be appreciated that other valve systems and other coupling arrangements may be used including, for example, those previously referenced. As such the invention is not intended to be limited to the specific valve system and mask described below.

Figure 3:
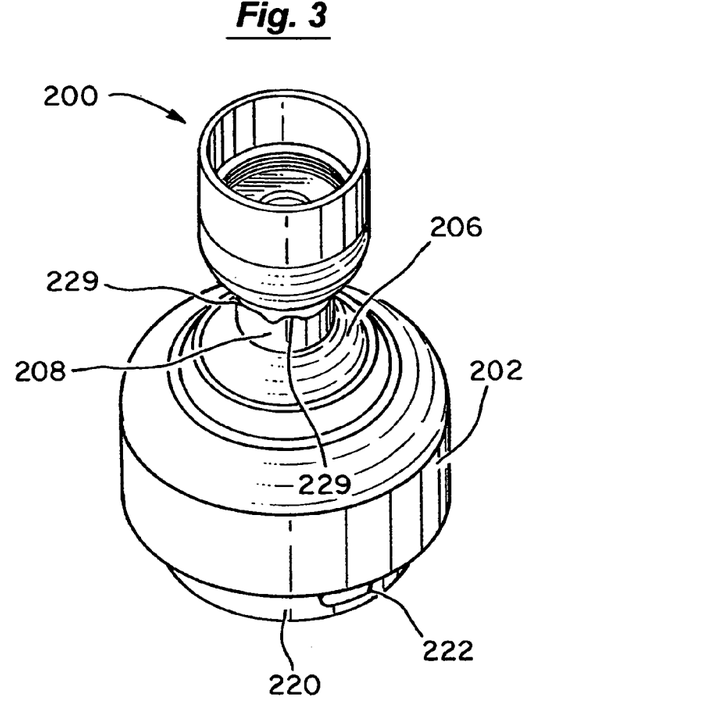
FIG. 3 is a perspective view of the valve system of FIG. 2.
Figure 4:
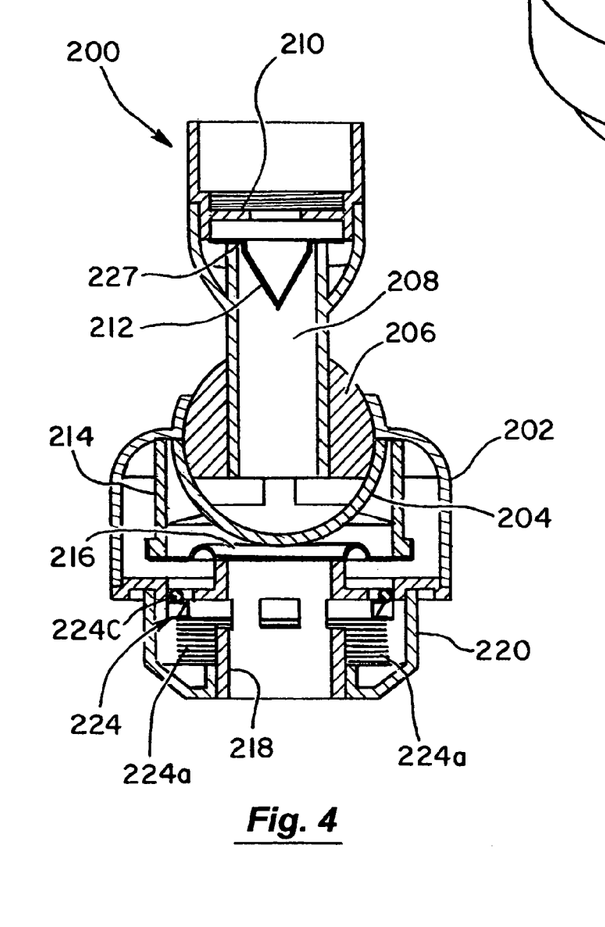
FIG. 4 is a cross sectional side view of the valve system of FIG. 3.
Figure 5:
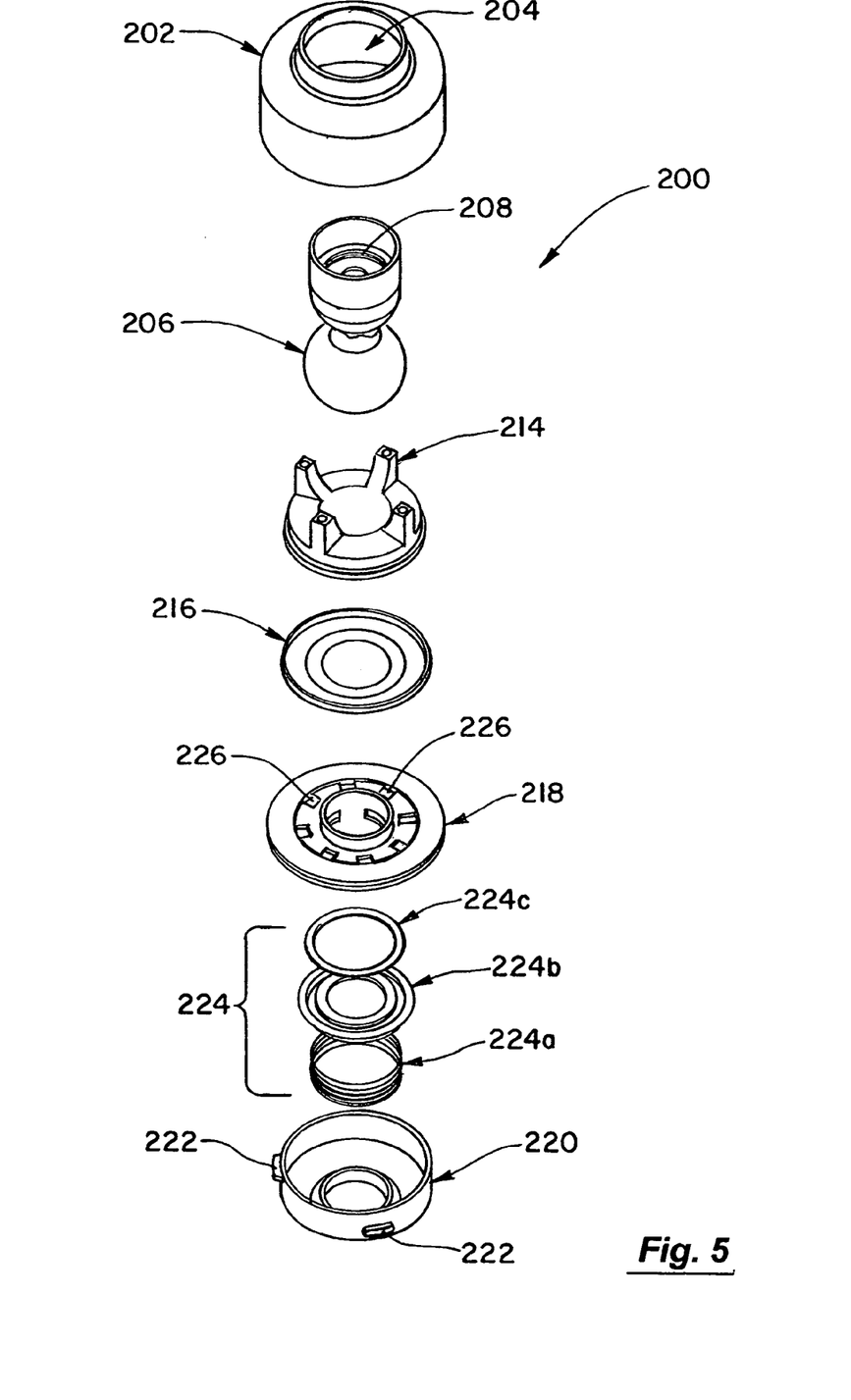
FIG. 5 is an exploded view of the valve system of FIG. 3.

Referring also to FIGS. 3-5, valve system 200 will be described in greater detail. Valve system 200 includes a valve housing 202 with a socket 204 into which a ball 206 of a ventilation tube 208 is received. In this way, ventilation tube 208 may rotate about a horizontal axis and pivot relative to a vertical axis. A respiratory source, such as a ventilation bag, may be coupled to tube 208 to assist in ventilation. Disposed in ventilation tube 208 is a filter 210 that is spaced above a duck bill valve 212. A diaphragm holder 214 that holds a diaphragm 216 is held within housing 202. Valve system 200 further includes a patient port 218 that is held in place by a second housing 220. Housing 220 conveniently includes tabs 222 to facilitate coupling of valve system 200 with facial mask 100. Also held within housing 220 is a check valve 224 that comprises a spring 224a, a ring member 224b, and an o-ring 224c. Spring 224a biases ring member 224b against patient port 218. Patient port 218 includes bypass openings 226 that are covered by o-ring 224c of check valve 224 until the pressure in patient port 218 reaches a threshold negative pressure to cause spring 224a to compress.

When the patient is actively ventilated, respiratory gases are forced through ventilation tube 208. The gases flow through filter 210, through duck bill valve 212, and forces up diaphragm 214 to permit the gases to exit through port 218. Hence, at any time the patient may be ventilated simply by forcing the respiratory gases through tube 208.

During the exhalation phase of a breathing cycle, expired gases flow through port 218 and lift up diaphragm 214. The gases then flow through a passage 227 in ventilation tube 208 where they exit the system through openings 229 (see FIG. 16).

During the inhalation phase of a breathing cycle, valve system 200 prevents respiratory gases from flowing into the lungs until a threshold of negative intrathoracic pressure level is exceeded. When this pressure level is exceeded, check valve 224 is pulled downward as springs 224a are compressed to permit respiratory gases to flow through openings 226 and to the patient's lungs by initially passing through tube 208 and duck bill valve 212. Valve 224 may be set to open when the negative intrathoracic pressure is in the range from about 0 cm H2O to about −50 cm H2O, and more preferably from about −5 cm H2O to about −30 cm H2O. Hence, the magnitude and duration of negative intrathoracic pressure may be enhanced during patient inhalation by use of valve system 200. Once the intrathoracic pressure falls below the threshold, recoil spring 224a again close check valve 224. In this way, circulation is increased to cause more blood to flow into the thorax and thereby increase vital organ perfusion. In so doing, the person's cardiovascular system is stressed in a convenient manner.

Figure 6:
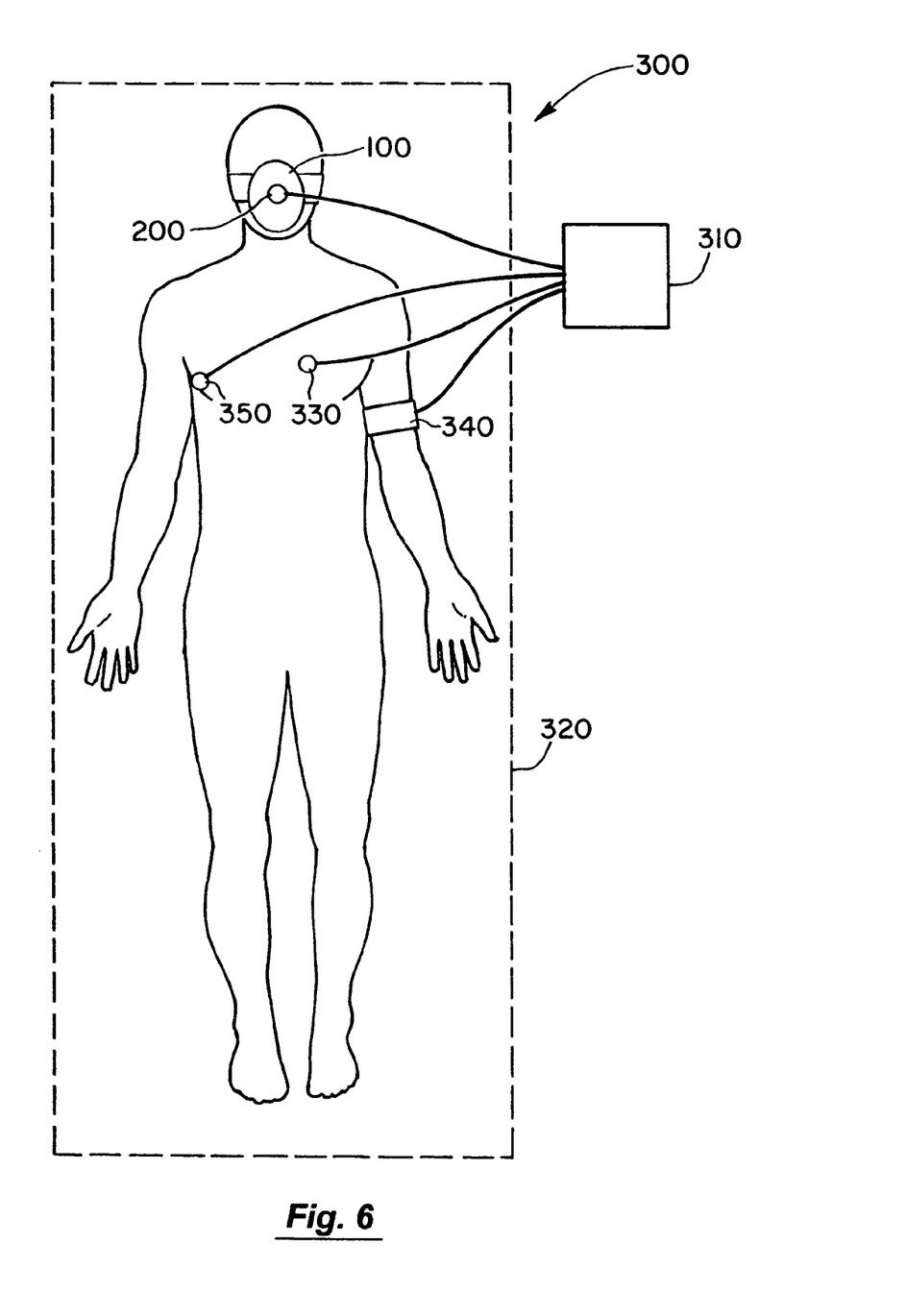
FIG. 6 is a schematic diagram of a system for diagnosing cardio-vascular-related conditions according to the invention.

Any of the valve systems described herein may be incorporated into a diagnostic system 300 as illustrated in FIG. 6. System 300 may conveniently include facial mask 100 and valve system 200, although any of the valve systems or interfacing mechanisms described herein or the like may be used. Valve system 200 may conveniently be coupled to a controller 310. In turn, controller 310 may be used to control the impedance level of valve system 200 in a manner similar to any of the embodiments described herein. The level of impedance may be varied based on measurements of physiological parameters, or using a programmed schedule of changes. System 300 may include a wide variety of sensors and/or measuring devices to measure any of the physiological parameters described herein. These sensors or measuring devices may be integrated within or coupled to valve system 200 or facial mask, or may be separate.

For example, valve system 200 may include a pressure transducer for taking pressure measurements (such as the intrathoracic pressures), a flow rate measuring device for measuring the flow rate of air into or out of the lungs, or a $CO_2$ sensor for measuring expired $CO_2$. As another example, system 300 may include an imaging device 320 for taking internal images of the person. Imaging device 320 may comprise a CT scanner, a MRI scanner, or the like. Other examples include equipment for producing echo images of the heart, such as ultrasonic transducers that are used either externally or internally within the heart. With such imaging devices, imaging may need to be gated based upon the respiratory rate, or motion associated with the change in position of the heart and other body structures. This may be accomplished using controller 310.

The use of valve system 200 permits the use of such imaging equipment because the person's cardiovascular system may be stressed without requiring the person to physically exercise. Instead, the person may sit or lie essentially motionless (except for breathing motion) and be imaged or have other measurements taken.

Examples of other sensors or measuring devices include a heart rate sensor 330, a blood pressure sensor 340, and a temperature sensor 350. These sensors may also be coupled to controller 310 so that measurements may be recorded. Further, it will be appreciated that other types of measuring devices may be used to measure various physiological parameters, such as oxygen saturation and/or blood levels of $O_2$, blood lactate, blood pH, tissue lactate, tissue pH and the like.

In some cases, controller 310 may be used to control valve system 200, to control any sensors or measuring devices, to record measurements, and to perform any comparisons. Alternatively, a set of computers and/or controllers may be used in combination to perform such tasks. This equipment may have appropriate processors, display screens, input and output devices, entry devices, memory or databases, software, and the like needed to operate system 300. For example, once measurements have been taken and recorded, controller 310 may access a database to obtain information on expected responses. Controller 310 may then perform a comparison to determine any differences and to recommend a possible diagnosis. This information may be stored in a patient record and may also be displayed to a physician and/or printed using a printer.

The invention has now been described in detail for purposes of clarity and understanding. However, it will be appreciated that certain changes and modifications may be practiced within the scope of the appended claims.

What is claimed is:

1. A method for diagnosing a cardiovascular-related condition in a breathing person, the method comprising:
   interfacing a valve system to the person's airway, the valve system being configured to decrease or prevent respiratory gas flow to the person's lungs during at least a portion of an inhalation event;
   permitting the person to inhale and exhale through the valve system, wherein during inhalation the valve system functions to produce a vacuum within the thorax to increase blood flow back to the right heart of the person, thereby increasing blood circulation and blood pressure;
   measuring at least one physiological parameter while the person inhales and exhales through the valve system, and evaluating the measured parameter to diagnose a cardiovascular condition.

2. A method as in claim 1, further comprising measuring the physiological parameter in a base line state prior to permitting the person to inhale and exhale through the valve system, and further comprising comparing the measured physiological parameter in the base line state with the measured physiological parameter following inhaling and exhaling.

3. A method as in claim 1, wherein the valve system is incorporated into a facial mask, and further comprising coupling the facial mask to the person's face.

4. A method as in claim 1, wherein the valve system include a pressure responsive inflow valve, and further comprising setting an actuating pressure of the valve to be in the range from about 0 cm $H_2O$ to about −50 cm $H_2O$.

5. A method as in claim 4, further comprising increasing or decreasing the actuating pressure over time, and re-measuring the physiological parameter.

6. A method as in claim 4, further comprising increasing or decreasing the actuating pressure based on the measured physiological parameter.

7. A method as in claim 1, wherein the valve system is further configured to prevent or decrease exhaled gases from exiting the person's lungs during at least a portion of an exhalation, and further comprising measuring the physiological parameter following an exhalation.

8. A method as in claim 1, wherein the physiological parameter is measured by an imaging or mapping technique.

9. A method as in claim 8, wherein the imaging or mapping technique is selected from a group consisting of ECG, echo-imaging of the heart, imaging of radio-labeled markers in the blood, MRI imaging, CT imaging and imaging of markers for cardiac ischemic.

10. A method as in claim 1, wherein the measured physiological parameter is selected from a group consisting of blood pressure, expired $CO_2$, heart rate, air flow and pressure through the airway and lungs, oxygen saturation, blood levels of $O_2$, blood lactate, blood pH, tissue lactate, tissue pH and body temperature.

11. A method as in claim 1, wherein the measured physiological parameter comprises one or more markers of cardiac ischemia.

12. A method as in claim 1, further comprising introducing a substance into the person to stress the person's heart.

13. A method as in claim 12, wherein the substance comprises a volume load of saline solution that is injected into the person's blood stream.

14. A method as in claim 12, wherein the substance comprises nitroglycerine that is injected into the person to lower the person's blood pressure.

15. A method as in claim 12, wherein the substance comprises a drug that is injected into the person and is selected from a group of drugs consisting of adenosine, adrenaline and dobutamine.

16. A system for diagnosing a cardiovascular-related condition in a breathing person, the system comprising:

a valve system that is capable of being coupled to the person's airway, the valve system being configured to decrease or prevent respiratory gas flow to the person's lungs during at least a portion of an inhalation event to produce a vacuum within the thorax to increase blood flow back to the right heart of the person, thereby increasing blood circulation and blood pressure; and a monitoring system to monitor changes in at least one physiological parameter while the person inhales and exhales through the valve system.

17. A system as in claim 16, wherein the monitoring system includes a computer for evaluating the measured parameter to diagnose a cardiovascular condition.

18. A system as in claim 16, wherein at least a portion of the monitoring system is physically incorporated into the valve system.

19. A system as in claim 16, further comprising a controller to change the configuration of the valve system over time to vary the level of inspiratory impedance.

20. A system as in claim 19, wherein the controller is configured to change the configuration of the valve system based on the measured parameters.

21. A system as in claim 16, wherein the valve system is configured to prevent or decrease exhaled gases from exiting the person's lungs during at least a portion of an exhalation.

22. A system as in claim 16, wherein the valve system is incorporated into a facial mask that is configured to be coupled to the person's face.

23. A system as in claim 16, wherein the valve system includes a pressure responsive inflow valve that has an actuating pressure in the range from about 0 cm $H_2O$ to about −50 cm $H_2O$.

24. A system as in claim 16, wherein the monitoring system comprises an imaging or mapping system.

25. A system as in claim 24, wherein the imaging or mapping system is selected from a group consisting of an ECG system, a heart echo-imaging system, a radio-labeled marker imaging system for measuring makers in the blood, an MRI imaging system, a CT imaging system and a cardiac ischemic imaging system.

26. A system as in claim 16, wherein the monitoring system comprises sensors that are selected from a group consisting of blood pressure sensors, expired $CO_2$ sensors, heart rate sensors, air flow and pressure sensors, oxygen saturation sensors, $O_2$ blood level sensors, blood lactate sensors, blood pH sensors, tissue lactate sensors, tissue pH sensors and body temperature sensors.

27. A method for diagnosing a cardiovascular-related condition in a breathing person, the method comprising:

interfacing a valve system to the person's airway, the valve system being configured to decrease or prevent respiratory gas flow to the person's lungs during at least a portion of an inhalation event;

coupling a monitoring system to the person, wherein the monitoring system is configured to monitor changes in at least one physiological parameter while the person inhales and exhales through the valve system;

permitting the person to inhale and exhale through the valve system, wherein during inhalation the valve system functions to produce a vacuum within the thorax to increase blood flow back to the right heart of the person, thereby increasing blood circulation and blood pressure;

measuring at least one physiological parameter while the person inhales and exhales through the valve system using the monitoring system, and evaluating the measured parameter to diagnose a cardiovascular condition.

* * * * *